(12) United States Patent
Caunce et al.

(10) Patent No.: US 8,061,215 B2
(45) Date of Patent: Nov. 22, 2011

(54) APPARATUS FOR AND METHOD OF MEASURING TENSION IN A HANDRAIL FOR AN ESCALATOR OR MOVING WALKWAY

(75) Inventors: A. Stuart Caunce, Cobourg (CA); Andrew O. Kenny, Toronto (CA); Michael Degli Angeli, Pickering (CA)

(73) Assignee: EHC Canada, Inc., Oshawa (CA)

( * ) Notice: Subject to any disclaimer, the term of this patent is extended or adjusted under 35 U.S.C. 154(b) by 175 days.

(21) Appl. No.: 12/138,863

(22) Filed: Jun. 13, 2008

(65) Prior Publication Data
US 2009/0308173 A1 Dec. 17, 2009

(51) Int. Cl.
*G01N 3/08* (2006.01)
(52) U.S. Cl. .......................................... 73/826
(58) Field of Classification Search ...................... 73/826
See application file for complete search history.

(56) References Cited

U.S. PATENT DOCUMENTS

| | | | | |
|---|---|---|---|---|
| 4,562,914 A * | 1/1986 | Boltrek | ......................... | 198/336 |
| 4,809,840 A * | 3/1989 | Nakatani | ......................... | 198/328 |
| 5,092,446 A * | 3/1992 | Sullivan et al. | ............... | 198/323 |
| 5,645,156 A * | 7/1997 | Zaharia et al. | ................ | 198/323 |
| 6,557,420 B1 * | 5/2003 | Garcia et al. | ..................... | 73/849 |
| 7,278,528 B2 * | 10/2007 | McLeod et al. | ............... | 198/337 |
| 7,407,477 B2 * | 8/2008 | Lamoureux | ........................ | 600/3 |
| 2003/0136635 A1 * | 7/2003 | Lauch | ........................... | 198/335 |

FOREIGN PATENT DOCUMENTS
CA 898726 A 4/1972

OTHER PUBLICATIONS

Schindler AG, Maintenance Manual.
Declaration of A. Stuart Caunce.

* cited by examiner

*Primary Examiner* — Lisa M Caputo
*Assistant Examiner* — Octavia Davis
(74) *Attorney, Agent, or Firm* — Bereskin and Parr LLP/S.E.N.C.R.L., s.r.l.

(57) ABSTRACT

An apparatus for and a method of measuring tension in a handrail for an escalator or moving walkway provides for three support or contact points on the handrail. Two outer or first and second support points are provided by rollers at either end of the support bar. A centre point is provided by a suction cup or other attachment device that grasps the handrail. The centre point is displaced relative to the first and second points by an amount less than a clearance between the handrail and an underlining guide. This displacement and the load necessary to cause the displacement, together with the overall dimensions of the apparatus enable the tension in the handrail to be provided. The use of a suction cup effectively overcomes the requirement to provide a centre point on the opposite side of the handrail from the two other support points, this other side not otherwise being accessible in use.

19 Claims, 4 Drawing Sheets

APPARATUS FOR AND METHOD OF MEASURING TENSION IN A HANDRAIL FOR AN ESCALATOR OR MOVING WALKWAY

FIELD

This invention relates to handrails for escalator and moving walkways. More particularly, this invention relates to a method of and an apparatus for measuring tension in a handrail.

BACKGROUND

Handrails for escalators, moving walkways and the like perform an important function and can serve as a safety component of the system. The handrail is required to provide a firm grip for the passenger and yet it has to be sufficiently flexible to bend around various drive wheel mechanisms and strong enough to withstand several tens of thousands of Newtons of tensile force.

Canadian Patent 898,726 discloses a widely used type of handrail construction having a standard C-shaped cross-section with longitudinally extending stretch inhibitor, body reinforcing fabric plies and a slider member, all joined together in a molded rubber composition. The stretch inhibitor is provided as an integral band of several steel wire cables which are embedded in a rubber body matrix. The wire cables are under tension and are sufficient in number to meet the load specification of approximately 30,000 Newtons tensile strength.

The handrail is often the single most expensive component to replace in an escalator or moving walkway, and the tension under which the handrail is run is one of the main variables that affect its life. The handrail forms an endless loop around the top and end surfaces of the balustrade of the escalator or moving walkway, commonly sliding on metal or plastic guides, and returns out of sight inside the balustrade or supporting structure, generally in line with the steps. It is on this return run that the drive mechanism of the handrail is placed. Most handrail drives require that there be no excessive slack in the handrail to avoid buckling and kinking of the handrail leading to damage, while excessive tension in the handrail leads to high friction forces on the guided portions of the unit and undue distortion of the flexible handrail around pulleys and roller clusters, leading to untimely wear and fatigue failure.

All escalators and moving walkways have some means of taking up excess slack in the handrail loop, by mechanically adjusting the length of the handrail path; such adjustment correspondingly adjusts the handrail tension, and accommodates increases or decreases in handrail length over its life. However, incorrect setting of this adjustment often leads to over-tensioning of the handrail resulting in over-heating of the handrail and reduced service life. Current methods used in the industry to judge the correct tension in the handrail are subjective and can require levels of skill and experience not always available. Some of the typical known methods (and figures showing these methods are described below) are:
  (i) The handrail is grasped by a technician at either of the newel ends and pulled in a normal, horizontal direction and the tension judged by distance the handrail moves.
  (ii) For an escalator, at the lower curve of the balustrade the tension normally lifts the handrail from its usual position sitting on top of the handrail guide. Pressing the handrail down at the centre of this curve until it sits back onto the guide allows a skilled mechanic to judge the handrail tension. This technique cannot be used on moving walkways.
  (iii) By dismantling part of the balustrade it is possible in some types of escalator to see the return run of the handrail and to judge by the amount of sag between two supporting points whether it is too tight or slack. This technique lacks precision and requires costly maintenance time.

None of these methods accurately and repeatably measure the actual tension in the handrail, although the assignee of the present invention has found that by employing a strain gauge to press the handrail down as in method (ii) it is possible to better compare handrail tensions between similar escalators using the same type of handrails (although this concept has not previously been publicly disclosed). As noted, this method is however limited to escalators and cannot be used on moving sidewalks which are horizontal and do not have suitable curves; they are also typically much longer than escalators and therefore more often exposed to incorrect tensioning.

Most devices available for measuring tension in elongate and flexible belts, films, fabrics etc. rely on the well known tensiometer which applies a force at the centre point on one side of the article, while supporting the article, between two supports on the opposite side of it. The force required to deflect the centre point relative to the support points is used to calculate the tension in the article. Typically these products are flat or rope-like enabling a device to contact both sides of the tensioned element or article, i.e. at the required centre and support points, at the same time. In such products, the actual tension elements comprise all or a substantial part of these products; in contrast, in a handrail, the stretch inhibitors or tension elements are embedded in the body of the handrail and are not readily accessible.

SUMMARY

In a handrail however, the present inventor has realized that the C shape of the product makes it impossible to access the tension elements directly, or even the flat portion of the handrail containing the tension elements without disassembly of the escalator.

It is desirable to enable accurate tension measurement of a handrail without its removal from any part of the escalator or moving walkway or without any disassembly of the steps, or panels of the balustrade.

As detailed below, an apparatus in accordance with the present invention utilizes the clearance in the vertical plane between a typical handrail guide and the inner surface of the handrail, usually approximately 3 mm.

The apparatus can just sit on the handrail on a flat portion of the balustrade and holds or maintains the handrail down against the guide using two rollers set a specific distance apart. Rollers may be used to allow longitudinal movement of the handrail while restricting any vertical movement. A suction cup or other device for grasping the handrail is used to grasp the handrail at the centre-point between the two rollers. The grasping device is attached to a strain gauge to enable a force applied by it to be measured. The required vacuum for the suction cup is supplied either by means of a separate pump or by mechanical means. The strain gauge and attached grasping device may be moved vertically by a lever or screw mechanism lifting the handrail at the centre-point off the handrail guide. The vertical movement of the handrail may be measured by means of a dial indicator or the like contacting the handrail surface close to the grasping device. The force required to move the handrail a predetermined distance, e.g. of approximately 2 mm, is recorded. The tension can then be calculated.

In accordance with a first aspect of the present invention, there is provided an apparatus for measuring tension in a handrail for use on an escalator or moving walkway, the apparatus comprising: an elongate support bar; first and second support points at either end of the bar for contacting and supporting the apparatus relative to the top surface of a handrail; an attachment device for attachment to the handrail at a centre point between the first and second support points; a displacement mechanism mounted between the support bar and the attachment device for displacing the attachment device and the centre point of the handrail relative to the first and second support points; a load measurement device for measuring a load applied to the attachment device to displace the centre point of the handrail; and a displacement measuring device for measuring the displacement of the centre point of the handrail relative to the first and second support points, for determining the tension in the handrail. A second aspect of the present invention provides a method of measuring tension in a handrail for use on an escalator or moving walkway, the method comprising the steps of: (1) providing the handrail on a handrail guide having a vertical clearance between the handrail and the guide, and selecting a length of the handrail including first and second support points and a centre point between the first and second support points where an inside top surface of the handrail is abutting the guide; (2) while maintaining the inside top surface of the handrail in abutment with the guide at the first and second support points, displacing the centre point relative to the guide by an amount less than the vertical clearance between the handrail and the guide whereby the handrail betweeen the first and second support points is substantially unsupported by the guide; (3) measuring the displacement of the centre point and the load required to effect that displacement; and (4) determining the tension in the handrail from the location of the first, second and centre support points, the displacement of the centre point and the load required to displace the centre point.

A further aspect of the present of the present invention provides a method of measuring tension in a handrail on an escalator, the method comprising: (1) locating a section of a handrail towards the lower end of escalator wherein an inclined portion of the handrail is adjacent a horizontal portion of the handrail; (2) determining parameters relevant to calculating tension, including the angle between the horizontal and inclined portions, the curvature of a handrail guide between the inclined and horizontal portions and the vertical clearance between the handrail guide and the handrail; (3) displacing a generally central location of the curve portion of the handrail towards the handrail guide by an amount less than the vertical displacement between the handrail and the handrail guide; (4) measuring at least one of the force required to cause that displacement and the value of the actual displacement.

BRIEF DESCRIPTION OF THE DRAWINGS

For a better understanding of the present invention and to show more clearly how it may be carried into effect, reference will now be made, by way of example, to the accompanying drawings in which.

DESCRIPTION

Figure 1:
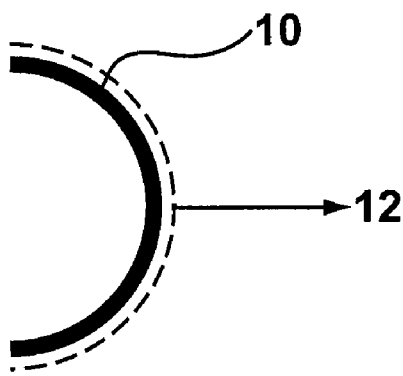
FIG. 1 is a schematic side view of a newel end of a handrail showing a conventional technique for checking tension.
Figure 2:
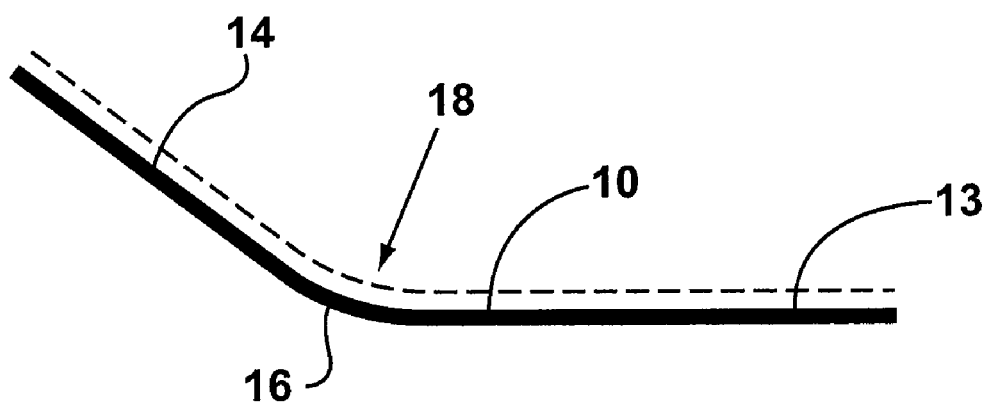
FIG. 2 is a perspective view of part of a handrail showing one technique for checking tension in a handrail according to the present invention.
Figure 3:
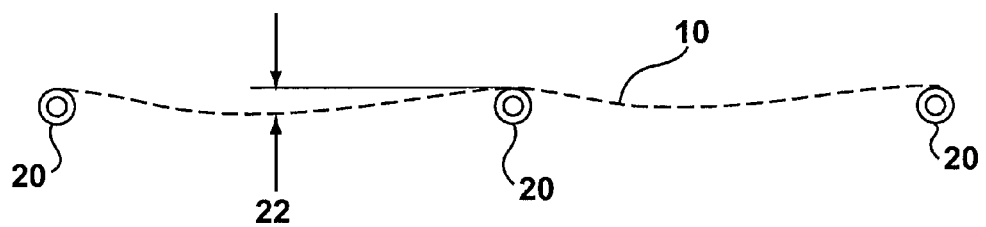
FIG. 3 is a schematic showing part of a return run of the handrail showing a further conventional technique for checking tension.

Referring first to FIGS. 1 and 3, these show conventional techniques for checking tension or slack in the handrail, as mentioned above, and in FIG. 2 a modification of an existing technique in accordance with the present invention.

With reference to FIG. 1, a handrail is indicated generally at 10. The newel end of the handrail can be checked for slack by pulling in the direction of the arrow 12. This presumes that rollers or other devices around the newel end of the handrail will permit the handrail to be pulled as far is as necessary to check the tension.

FIG. 2 shows a side view of the bend that is found at the bottom end of any conventional escalator, where the handrail, again indicated at 10 has a horizontal portion 13 and an inclined portion 14. At a bend 16 between these horizontal and inclined portions 13, 14, the handrail will tend to lift up from the handrail guide. By pushing in the direction of the arrow 18, the tension in the handrail can be judged.

Figure 6:
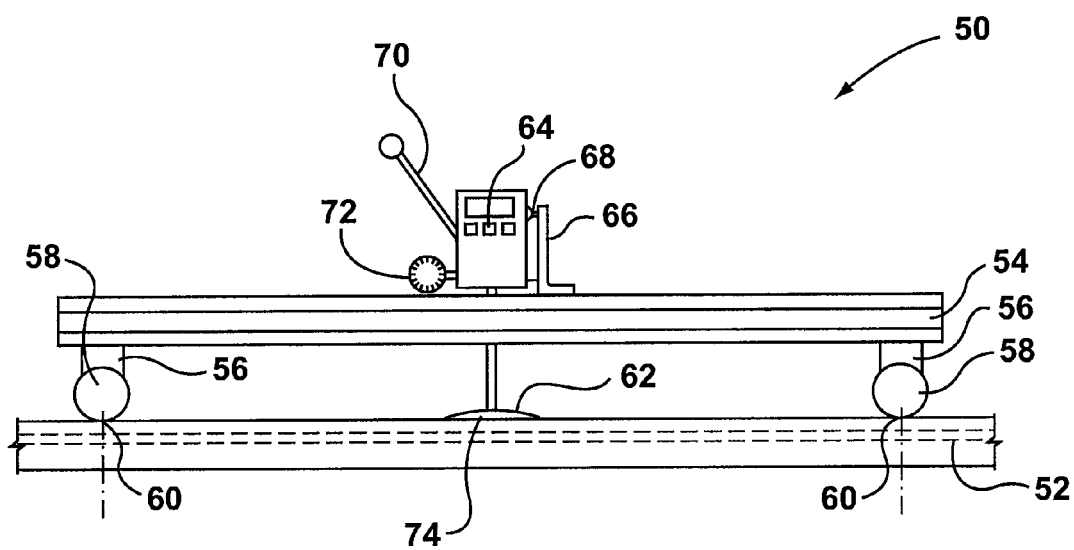
FIG. 6 is a side view of an apparatus in accordance with the present invention.

In accordance with the present invention, the force and/or displacement of the handrail, indicated by arrow 18, can be measured by suitable measurement devices, e.g. as shown in FIG. 6, to provide a quantitative measurement. Practically, to obtain meaningful data and to compare data and to compare data between handrails, it will be necessary to know the angle of the inclined portion 14, the radius of the curved portion between the straight and inclined portions 13, 14, and usually some data on the characteristics of the handrail (weight per unit length, stiffness, etc.).

Referring to FIG. 3, on the return run of a handrail, below an escalator or moving walkway, the handrail 10 is often supported at spaced locations by rollers 20, so as to leave spans of the handrail between pairs of rollers 20 unsupported. Consequently, as indicated at 22, there will be some sag in each span of the handrail between adjacent pairs of rollers 20. If this sag 22 is measured, this can be used as a measure of the tension in the handrail 10.

Figure 4:
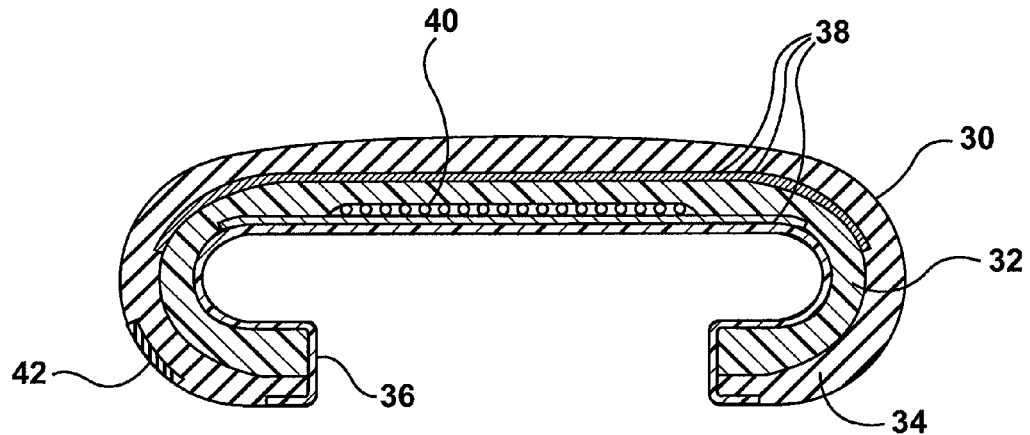
FIG. 4 is a cross-section through a conventional handrail.

FIG. 4 shows an exemplary handrail structure. It will be understood that the present invention is applicable to any type of handrail. The handrail can have a body that is a uniform composition, or a body that is formed from two or more different types of material. Further, the body can be formed from either a thermoset or a thermoplastic material.

In FIG. 4, the handrail is indicated generally at 30 and comprises a body formed from an inner carcass layer 32 and an outer cover layer 34 of a thermoset or rubber material. This handrail 30 is a rubber handrail with a carcass that consists of layers of rubber and fabric. Each layer under the cover rubber is referred to as a body ply. In known manner, a slider material, e.g. a woven nylon slider is provided at 36 around the interior of the C-shaped cross-section of the handrail. The body plies are indicated at 38 and steel wire stretch inhibitors are provided at 40. A brand identifier can be provided at the location indicated at 42.

Figure 5:
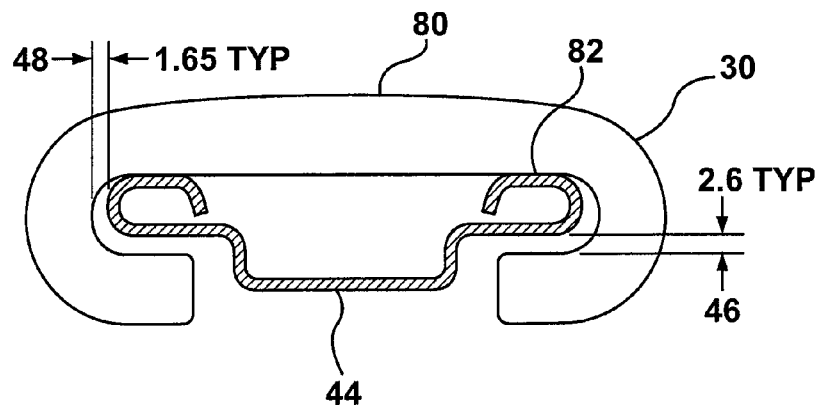
FIG. 5 is a schematic cross-section through a conventional handrail and a handrail guide showing spacing between them.

Turning to FIG. 5, the handrail 30 is indicated in schematic outline, and is shown mounted on a guide indicated at 44. In known manner, to accommodate tolerances in manufacture and to avoid unnecessary contact between the guide and the handrail, substantial clearances are usually provided between the handrail and the guide. Additionally, manufacture of the handrail is usually done independently from the design and construction of the escalator or moving walkway, which also promotes the use of generous tolerances. As indicated, a vertical clearance 46 and a horizontal clearance 48 are provided (for clarity, the handrail 30 is shown centered on the guide 44 with small horizontal clearances on both sides; the indicated clearance 48 is intended to represent one half of the total horizontal clearance). Typical dimensions for these clearances are 2.6 mm for the vertical clearance and 1.65 mm for the horizontal clearance 48, and again these will vary depending upon the guide and the handrail 30, and can vary between different manufacturers.

Turning to FIG. 6, this shows an apparatus 50 in accordance with the present invention, shown mounted on a handrail, here indicated at 52. The apparatus 50 has a main support bar 54 that can be formed from an elongated extruded aluminum section. The support bar 54 should be lightweight and rigid, as detailed below; when subject to the load of lifting the centre portion of the handrail, its deflection should not affect the measurement of the handrail deflection.

At either end of the support bar 54, there are short downwardly extending support legs 56, at the lower end of each of which there is mounted a roller 58. The rollers 58 contact the top of the handrail 52 at first and second support points 60. For some applications rollers may be unnecessary. They ensure that the handrail is free to move in a longitudinal direction while a central point is lifted up by a small amount. It may not always be necessary to allow for this movement. Alternatives to rollers can also be used, such as a low friction material on the bottom of the legs 56 or some elements that can pivot by a small amount to permit the longitudinal motion, without necessarily being capable of full rotation.

At the center of the support bar 54, there is a suction cup 62 that provides an attachment device for grasping or attaching to the handrail 52. The suction cup 62 is connected to a load cell 64, providing a load measuring device for measuring the load applied to the suction cup 62. The load cell 64 is mounted by a linear bearing or the like 68 to a mounting bracket 66 attached to the top of the support bar 54. A lever mechanism 70, as a displacement mechanism, is provided for displacing the load cell 64 with the suction cup 62 vertically upwards. The load cell 64 measures the vertical load applied to the suction cup 62. The suction cup is attached to a centre point 74 of the handrail 52.

A dial indicator 72, as a displacement measuring device, is provided for measuring the vertical displacement of the load cell 64 and hence of the suction cup 62. Practically, where a suction cup is used, there is significant movement between the top of the cup 62 and the handrail, so that measurement of the displacement generated by the lever mechanism does not accurately indicate vertical movement of the handrail 52. In such a case, it is believed that the only accurate way is to measure movement of the actual handrail 52 is directly by, for example, a dial gauge contacting the top of the handrail 52.

In use, a suitable flat section of the handrail 52 is selected. The apparatus 50 is placed on it so as to be supported by the rollers 58.

The suction cup 62 is then lowered and actuated so as to be attached by vacuum, to the relatively flat top surface of the handrail 52 at the centre point 74, as indicated at 80 in FIG. 5, with an inside top surface 82 resting on the guide 44. The vacuum can be created by a separate vacuum source or a simple manual device attached to the vacuum cup 62 in known manner. At this time, either the dial indicator 72 is set to a zero setting, or its initial reading is noted.

The lever mechanism 70 is then used to lift the center point 74 of the handrail by a known, preset amount. This preset amount is determined to be comfortably within the maximum limit of the vertical clearance 46 between the handrail 30, 52 and its guide 44, as shown in FIG. 5. Once this vertical limit is reached, the lever mechanism 70 can be such as to hold the handrail 52 in a fixed position, while a measurement is taken, although this is not essential.

At this time, with the center point 74 lifted by the preset amount, the vertical load recorded by the load cell 64 is noted.

It is to be noted that, during this process, the rollers 58 ensure that no additional tensile loads are applied to the handrail. The handrail is free to move in a longitudinal direction underneath the rollers 58. Also, the handrail is sufficiently heavy and flexible that it will not lift off the guide 44 at the support points 60.

Figure 7:
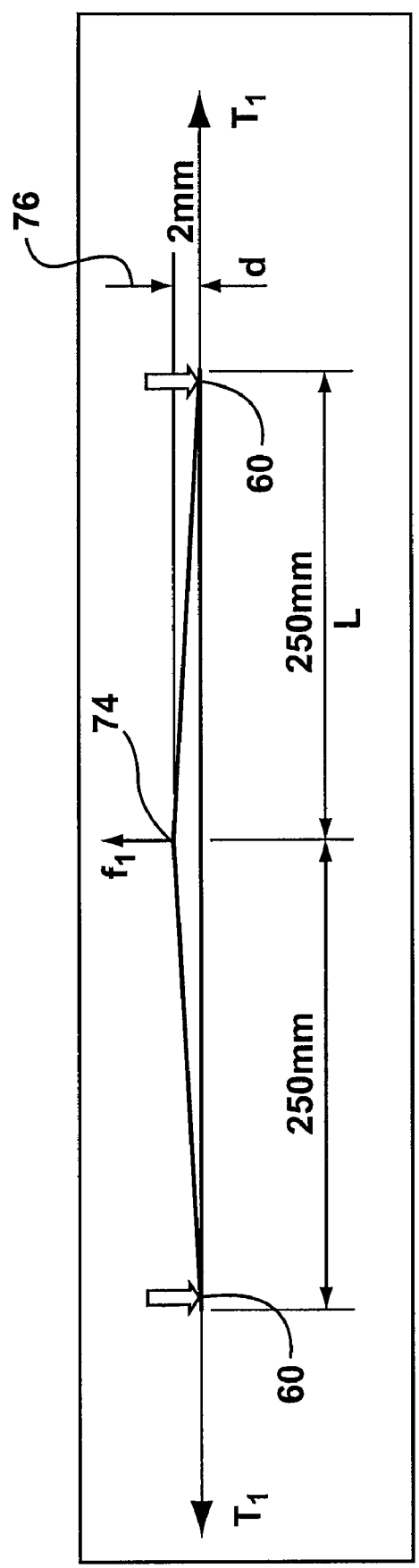
FIG. 7 is a schematic diagram showing analysis of operation of the apparatus of FIG. 6.

Referring now to FIG. 7, this shows a schematic of the handrail after the centre point 74 has been lifted as described above. The first and second support points 60 and the centre support point 74 are shown in FIG. 7. Also indicated at 76 is the preset displacement of the centre point 74 in a vertical direction. In this example, the centre point 74 is spaced from each of the first and second support points 60 by 250 mm, and the preset vertical displacement is 2 mm. The tension in the handrail is then calculated according to the following formula:

$$T_1 = \frac{L}{(d)} \times (f_1 - K).$$

Here, the parameters are:
$T_1$ = tension in the handrail
$f_1$ = vertical load applied to centre point 74
L = distance between centre point and each support point 60
d = displacement of centre point 74
K = constant In this example, L=250 mm and d=2 mm, so the formula reduces to: $T_1 = 125(f_1 - K)$ It will be understood that this formula is based on a simplification and assumes that the vertical displacement is small compared to the spacing between the support points.

The constant K depends upon the type and size of handrail, and will be related to the weight per unit length and the stiffness of the handrail.

As noted above, the problem with measuring the tension in a handrail is that the stretch inhibitor, usually steel cables or steel tape, is not directly accessible. As also noted above, a known technique for measuring tension in an elongate, flexible element, is to provide two support points and then to deflect the element between those two support points; from the deflection of the centre point and the load required to generate this deflection, the tension can be calculated. What the present inventor has realized is that, with the technique of the present invention, it is possible to apply this technique to a handrail.

Thus, the two support points are provided at 60 by the rollers 58. Since it is not possible to access the opposite or underside of the handrail to provide the third support point, the present invention provides the suction cup 62. This essential recognizes that the handrail, by itself, is flexible but at the same time the body of the handrail is relatively rigid. Thus, adhering the suction cup to the top surface 80 has the same material effect as supporting the handrail on the inside top surface 82, i.e. contacting the stretch inhibitor at the centre point 74; in other words, any elastic deformation between the top surface 80 and the underlying stretch inhibitor will be immaterial, and likely not even capable of measurement. This arrangement then simulates the three point contact arrangement necessary to determine the tension in the handrail.

It may be that the apparatus 50 will be sufficiently heavy to maintain the handrail in contact with the guide 44 at the support points 60. However for some applications, it may be necessary or desirable to ensure that the apparatus is held down, to ensure that there is no lifting of the handrail at the support points 60.

It is also recognized that, while a vacuum cup 62 may have advantages, there may be other suitable methods of grasping the handrail 52 at the centre point 74. Thus, while the lips of the handrail around the C-shaped cross-section have a certain flexibility, there may be techniques for mechanically grasping the handrail in a manner that prevents, or at least sufficiently minimizes, any mechanical deflection of components of the handrail which would tend to give a false reading of the deflection of the stretch inhibitor at the centre point 74. Such alternative methods of grasping and displacing the handrail 52 may avoid the disadvantages of a vacuum cup 62, so that measurement of the movement of the grasping device will, with sufficient accuracy, indicate the displacement of the handrail 52.

The invention claimed is:

1. An apparatus, for measuring tension in a handrail for use on an escalator or moving walkway, the apparatus comprising:
   an elongate support bar;
   first and second support points at either end of the bar for contacting and supporting the apparatus relative to the top surface of a handrail;
   an attachment device for attachment to the handrail at a centre point between the first and second support points;
   a displacement mechanism mounted between the support bar and the attachment device for displacing the attachment device and the centre point of the handrail relative to the first and second support points;
   a load measurement device for measuring a load applied to the attachment device to displace the centre point of the handrail; and
   a displacement measuring device for measuring the displacement of the centre point of the handrail relative to the first and second support points, for determining the tension in the handrail.

2. An apparatus as claimed in claim 1 including rollers at either end of the support bar, providing the first and second support points, and for permitting longitudinal motion of the handrail relative to the support bar.

3. An apparatus as claimed in claim 2, wherein the rollers are provided on support legs extending from the support bar.

4. An apparatus as claimed in claim 2, wherein the attachment device comprises a suction cup for attachment to a top surface of the handrail by a vacuum.

5. An apparatus as claimed in claim 2, wherein the load measuring device is connected to the attachment device, wherein a bearing is providing between the load measuring device and the support bar for enabling relative linear motion therebetween, and wherein the displacement mechanism is provided between the load measurement device and the support bar for displacing the load measuring device and the attachment device relative to the support bar.

6. An apparatus as claimed in claim 5, wherein the mechanism comprises a lever mechanism.

7. An apparatus as claimed in claim 6, wherein the displacement measuring device comprises a dial gauge.

8. An apparatus as claimed in claim 7, wherein the dial gauge is adapted to contact a top surface of the handrail to measure displacement thereof directly.

9. An apparatus as claimed in claim 6, wherein the rollers are mounted on legs connected to either end of the support bar and wherein the attachment device comprises a vacuum suction cup.

10. A method of measuring the tension in a handrail for use on an escalator or moving walkway, the method comprising the steps of:
    (1) providing the handrail on a handrail guide having a vertical clearance between the handrail and the guide, and selecting a length of the handrail including first and second support points and a centre point between the first and second support points where an inside top surface of the handrail is abutting the guide;
    (2) while maintaining the inside top surface of the handrail in abutment with the guide at the first and second support points, displacing the centre point relative to the guide by an amount less than the vertical clearance between the handrail and the guide whereby the handrail between the first and second support points is substantially unsupported by the guide;
    (3) measuring the displacement of the centre point and the load required to effect that displacement; and
    (4) determining the tension in the handrail from the location of the first, second and centre support points, the displacement of the centre point and the load required to displace the centre point.

11. A method as claimed in claim 10, comprising selecting a straight, section of the handrail to provide the first support, second support and centre points.

12. A method as claimed in claim 11, including displacing the centre point of the handrail by an attachment device for grasping the handrail.

13. A method as claimed in claim 12, wherein the attachment device comprising a vacuum cup and the method includes, bringing the vacuum cup into abutment with a top surface of the handrail and applying a vacuum thereto to cause attachment to the vacuum cup to the top surface of the handrail.

14. A method as claimed in claim 11, including measuring the load and the displacement of the centre point with an apparatus including rollers that contact the handrail at the first and second support points, while permitting free longitudinal movement of the handrail.

15. A method as claimed in claim 14, including providing the apparatus with a support bar, mounting rollers on the support bar, providing a load cell for measuring the load applied to the attachment device and displacing the load cell and the attachment device relative to the support bar.

16. A method as claimed in claim 15, further including measuring the displacement of the load cell relative to the support bar to determine the displacement of the centre point of the handrail.

17. A method as claimed in claim 15 further including measuring the displacement of the handrail relative to the handrail under the support points.

18. A method as claimed in claim 10, wherein the tension of the handrail is calculated according to the following formula:

$$T_1 = \frac{L}{(d)} \times (f_1 - K)$$

wherein $T_1$ is the tension to be measured in the handrail, $f_1$ is the vertical load applied to the centre point of the handrail, L is the distance between the centre point and each of the first and second support points, d is the displacement of the centre point, and K is a constant.

19. A method as claimed in the claim 18, including calculating the tension of the handrail from one or more of: the angle between the horizontal and curved portions of the handrail; the curvature of the handrail guide; characteristics of the handrail, including weight per unit length and stiffness; force required to displace the handrail; and the magnitude of the displacement of the handrail towards the handrail guide.

* * * * *